US008642645B2

(12) United States Patent
Kelly

(10) Patent No.: US 8,642,645 B2
(45) Date of Patent: Feb. 4, 2014

(54) PHARMACEUTICAL COMPOSITION COMPRISING CANNABINOIDS

(75) Inventor: Brooks J. Kelly, Longmont, CO (US)

(73) Assignee: Brooks Kelly Research, LLC., Louisville, CO (US)

( * ) Notice: Subject to any disclaimer, the term of this patent is extended or adjusted under 35 U.S.C. 154(b) by 0 days.

(21) Appl. No.: 13/361,718

(22) Filed: Jan. 30, 2012

(65) Prior Publication Data

US 2012/0295968 A1  Nov. 22, 2012

Related U.S. Application Data

(60) Provisional application No. 61/583,664, filed on Jan. 6, 2012, provisional application No. 61/491,265, filed on May 30, 2011, provisional application No. 61/490,108, filed on May 26, 2011, provisional application No. 61/488,622, filed on May 20, 2011.

(51) Int. Cl.
*A61K 31/35* (2006.01)
*A61K 31/685* (2006.01)
*A61K 31/34* (2006.01)
*A61K 36/06* (2006.01)
*A61K 36/81* (2006.01)

(52) U.S. Cl.
USPC ........ 514/454; 514/78; 514/474; 424/195.15; 424/760

(58) Field of Classification Search
USPC ................ 514/454, 474, 78; 424/195.15, 760
See application file for complete search history.

(56) References Cited

U.S. PATENT DOCUMENTS

| | | | |
|---|---|---|---|
| 3,301,746 A | 1/1967 | Sanford et al. | |
| 3,812,000 A | 5/1974 | Salvucci et al. | |
| 3,814,096 A | 6/1974 | Weiss et al. | |
| 3,896,807 A | 7/1975 | Buchalter | |
| 3,974,025 A | 8/1976 | Ayers | |
| 4,112,167 A | 9/1978 | Dake et al. | |
| 4,191,609 A | 3/1980 | Trokhan | |
| 4,208,459 A | 6/1980 | Becker et al. | |
| 4,300,981 A | 11/1981 | Carstens | |
| 4,637,859 A | 1/1987 | Trokhan | |
| 4,690,821 A | 9/1987 | Smith et al. | |
| 4,798,603 A | 1/1989 | Meyer et al. | |
| 4,962,133 A | 10/1990 | Chromecek et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,221,534 A | 6/1993 | DesLauriers et al. | |
| 5,509,915 A | 4/1996 | Hanson et al. | |
| 5,520,917 A | 5/1996 | Mizuguchi et al. | |
| 5,525,345 A | 6/1996 | Warner et al. | |
| 5,612,045 A | 3/1997 | Syverson | |
| 5,624,676 A | 4/1997 | Mackey et al. | |
| 5,705,164 A | 1/1998 | Mackey et al. | |
| 5,716,692 A | 2/1998 | Warner et al. | |
| 5,720,966 A | 2/1998 | Ostendorf | |
| 5,843,056 A | 12/1998 | Good et al. | |
| 5,855,999 A | 1/1999 | McCormack | |
| 5,879,341 A | 3/1999 | Odorzynski et al. | |
| 6,063,335 A | 5/2000 | Pirolo et al. | |
| 6,146,648 A | 11/2000 | Bret et al. | |
| 6,149,934 A | 11/2000 | Krzysik et al. | |
| 6,179,961 B1 | 1/2001 | Fick et al. | |
| 6,211,139 B1 | 4/2001 | Keys et al. | |
| 6,217,890 B1 | 4/2001 | Paul et al. | |
| 6,238,682 B1 | 5/2001 | Klofta et al. | |
| 6,261,580 B1 | 7/2001 | Lehrter et al. | |
| 6,287,581 B1 | 9/2001 | Krzysik et al. | |
| 6,340,467 B1 | 1/2002 | Morrison | |
| 6,410,039 B1 | 6/2002 | Walker | |
| 6,428,794 B1 | 8/2002 | Klofta et al. | |
| 6,433,068 B1 | 8/2002 | Morrison et al. | |
| 6,458,343 B1 | 10/2002 | Zeman et al. | |
| 6,503,412 B1 | 1/2003 | Schroeder | |
| 6,503,526 B1 | 1/2003 | Krzysik et al. | |
| 6,534,074 B2 | 3/2003 | Krzysik et al. | |
| 6,570,054 B1 | 5/2003 | Gatto et al. | |
| 6,586,652 B1 | 7/2003 | Roe et al. | |
| 6,627,787 B1 | 9/2003 | Roe et al. | |
| 6,630,507 B1 | 10/2003 | Hampson et al. | |
| 6,716,204 B1 | 4/2004 | D'Acchioli et al. | |
| 6,733,772 B1 | 5/2004 | Bret et al. | |
| 6,825,393 B2 | 11/2004 | Roe et al. | |
| 7,105,685 B2 | 9/2006 | Travis | |
| 7,109,245 B2 | 9/2006 | Kunos et al. | |
| 7,547,443 B2 | 6/2009 | Krzysik et al. | |
| 2001/0014350 A1 | 8/2001 | Krzysik et al. | |
| 2002/0128615 A1 | 9/2002 | Tyrrell et al. | |
| 2002/0128621 A1 | 9/2002 | Kruchoski et al. | |
| 2002/0136755 A1 | 9/2002 | Tyrrell et al. | |
| 2002/0165508 A1 | 11/2002 | Klofta et al. | |
| 2004/0138293 A1* | 7/2004 | Werner et al. ................. | 514/454 |
| 2005/0058669 A1 | 3/2005 | Krzysik et al. | |
| 2011/0257256 A1 | 10/2011 | Fuchs et al. | |

FOREIGN PATENT DOCUMENTS

WO     2010/012506 A1    2/2010

* cited by examiner

*Primary Examiner* — Kevin E Weddington
(74) *Attorney, Agent, or Firm* — Kevin H. Fortin

(57) ABSTRACT

The present invention relates to a pharmaceutical composition comprising Δ9 Tetrahydrocannabinol (THC), Cannabidiol (CBD), and at least one small molecule selected from Citric Acid, Ascorbic Acid, Citrus Essential Oil(s), Lecithin, one or more sugar(s), Resvertrol, and combinations thereof, wherein the composition exhibits an increased but negated psychoactivity with concurrent enhancement in therapeutic potency of THC and/or CBD. The present invention is further directed to methods of treating one or more disease(s) or disorder(s) modulated by the activation of the Cannabinoid CB1 and/or CB2 receptors, by administering a therapeutically effective amount of the composition of the present invention to a subject in need thereof.

5 Claims, 2 Drawing Sheets

PHARMACEUTICAL COMPOSITION COMPRISING CANNABINOIDS

PRIORITY CLAIM

This invention claims priority to earlier filed provisional patent application Nos. 61/583,664, filed 6 Jan. 2012; 61/491,265, filed 22 Jun. 2011; 61/490,108, filed 3 Jun. 2011; 61/488,622, filed 20 May 2011, the disclosures of each of these provisional patent applications are incorporated herein by reference.

FIELD OF THE INVENTION

The present invention pertains to a pharmaceutical composition comprising Δ9 Tetrahydrocannabinol (THC), Cannabidiol (CBD), and at least one small molecule selected from Citric Acid, Ascorbic Acid, Citrus Essential Oil(s), Lecithin, one or more sugar(s), Resvertrol, and combinations thereof.

BACKGROUND OF THE INVENTION

Cannabinoids are a group of chemicals from *Cannabis Sativa* or *Cannabis indica* plant that are known to activate cannabinoid receptors (CB1 and CB2) in cells. These chemicals are also produced endogenously in humans and other animals and are termed endocannabinoids. Synthetic cannabinoids are manmade chemicals with the same structure as plant cannabinoids or endocannabinoids. Cannabinoids are cyclic molecules exhibiting particular properties such as the ability to easily cross the blood-brain barrier, weak toxicity and few side effects.

Δ9-Tetrahydrocannabinol (THC), represented by Formula (a), is the main psychoactive cannabinoid produced by the *Cannabis* Species which is well characterized for its biological activity and potential therapeutic application in a broad spectrum of diseases.

Cannabidol (CBD), represented by Formula (b), is another major constituent of Cannabinoids. CBD acts as an inverse agonist of the $CB_1$ and $CB_2$ cannabinoid receptors. CBD is a phytocannabinoid which unlike THC does not produce the psychoactive effects in humans. CBD is reported to exert analgesic, antioxidant, anti-inflammatory, and immunomodulatory effects.

The use of *Cannabis* as a medicine has been known since antiquity, but until recent times administration of complex *Cannabis* preparations (such as containing both THC and CBD) could only be achieved by delivery in ethanol or edible oils which were swallowed, or by the patient inhaling the vapors of *Cannabis* by smoking the dried plant material. Further, the psychoactive activity of THC has led to reluctance of public acceptance of medicines including this compound.

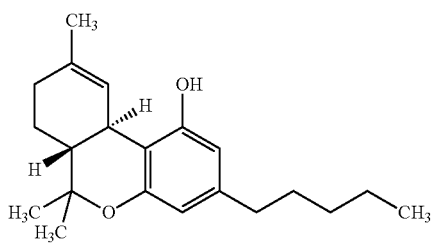

Formula a

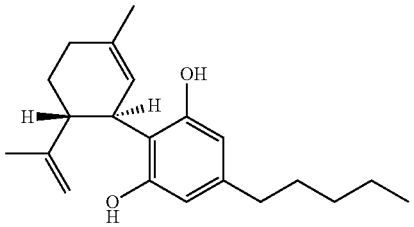

Formula b

THC may exist in a decarboxylated form or in a non-decarboxylated, Tetrahydrocannbinolic acid (THCA) form (FIG. 2). The decarboxylated form after consumption is extremely psychoactive whereas the non-decarboxylated form after consumption is drastically-less psychoactive. Fully-decarboxylated THC, the main psychotropic component of *Cannabis* sativa, is much more psychoactive when consumed in its fully-decarboxylated form as opposed to when it is consumed in its non-decarboxylated form. After consumption, fully-decarboxylated THC formulated in conjunction with CBD exhibits a plethora of complex actions including psychoactivity, anti-convulsivity, sedative, hypnotic, anti-nausea, and anti-hyperalgesic properties (Mechoulam et al., 2002; Costa et al., 2007). THC in conjunction with CBD can also reduce some types of inflammation, the complex biological response organs, tissues and cells have to harmful stimuli such as pathogens, damage, or irritants. The use of the formulations based on fully-decarboxylated THC with CBD is of significant interest because these formulations function as unique high-potency cannabinoid receptor agonists for both cannabinoid CB1 and CB2 receptors (Pertwee et al., 2007).

The Cannabinoids and the THC-CBD combinations have been known in the art for treating or preventing a number of diseases or disorders. For example, U.S. Pat. No. 6,630,507 discloses Cannabinoids for use as anti-oxidants and neuro-protectants; U.S. Pat. No. 7,105,685 discloses Cannabinoids for the treatment of diseases associated with immune dysfunction, particularly HIV disease and neoplastic disorders; U.S. Pat. No. 7,109,245 discloses Cannabinoids useful as vasoconstrictors; US Patent Publication US20110257256 discloses THC-CBD composition for use in treating or preventing Cognitive Impairment and Dementia; PCT Publication WO/2009/147439 discloses use of a combination THC and CBD in the manufacture of a medicament for use in the treatment of cancer, in particular the glioma tumour; PCT Publication WO/2007/148094 discloses use of THC-CBD composition for the treatment of neuropathic pain; and US Patent Publication US20100286098 discloses a method of treating tissue injury in a patient with colitis administering the THC-CBD combination.

Surprisingly, the Applicant of the present invention has found that a novel composition comprising fully decarboxylated THC and CBD along with one or more small molecule(s) such as citric acid, ascorbic acid, sugar(s), greatly enhances the therapeutic potency of THC while exploiting a concurrent enhancement in its psychoactivity which is fully negated relative to perception in vivo by counter balance by inclusion of CBD.

Till date, no one has disclosed a finding of a relationship regarding psychoactivity in fully-decarboxylated THC and the compositions of THC, CBD, and one or more small molecules as described hereinafter, which has greatly enhanced pharmacological action and exhibited an increased but negated psychoactivity.

There is thus an unmet need for exploiting enhanced therapeutic potential and psychoactivity of THC for the treatment or prevention of one or more disease(s) or condition(s) modulated by the activation of the Cannabinoid CB1 and/or CB2 receptors. The present invention satisfies these needs, as well as others.

SUMMARY OF THE INVENTION

The present invention pertains to a pharmaceutical composition comprising therapeutically effective amount of fully decarboxylated Δ9 Tetrahydrocannabinol (THC), Cannabidiol (CBD), and at least one small molecule, in selected ratios by weight, wherein the wherein the composition exhibits an increased but negated psychoactivity with concurrent enhancement in therapeutic potency of THC and/or CBD.

In one aspect, the at least small molecule as used in the composition of the present invention is selected from a group comprising of Citric Acid, Ascorbic Acid, Citrus Essential Oils (for example Orange Essential Oil, Tangerine Essential Oil, Grapefruit Essential Oil, Lime Essential Oil, Lemon Essential Oil and the like), lecithin, one or more sugars (for example glucose, fructose and the like), Resvertrol, or combinations thereof.

In one aspect, the present invention provides a method of treating one or more disease(s) or disorder(s) modulated by the activation of the Cannabinoid CB1 and/or CB2 receptors, by administering a therapeutically effective amount of the composition of the present invention to a subject in need thereof.

In another aspect, the present invention provides a method of treating/preventing/ameliorating a disease, disorder or condition selected from a group comprising of pain, cancer, pain, cancer, glaucoma, HIV, neurodegeneration, Alzheimer's disease, Parkinson's disease, multiple sclerosis, psychosis, anorexia/cachexia, nausea, hepatitis B, depression, anxiety, paraplegia, rheumatoid arthritis, sleeplessness, epilepsies, neurological movement disorders, inflammation, Crohn's diseases, ulcerative colitis, arthritis, neurodermatitis cognitive impairment, dementia, diabetes mellitus and hypertension, comprising administering a therapeutically effective amount of the composition of the present invention.

In a further aspect, the present invention provides methods of preparation of the compositions of the present invention including use in capsules, pills, nasal sprays, syrups, topical salves, eye drops and other delivery modalities.

DETAILED DESCRIPTION OF THE INVENTION

Figure 1:
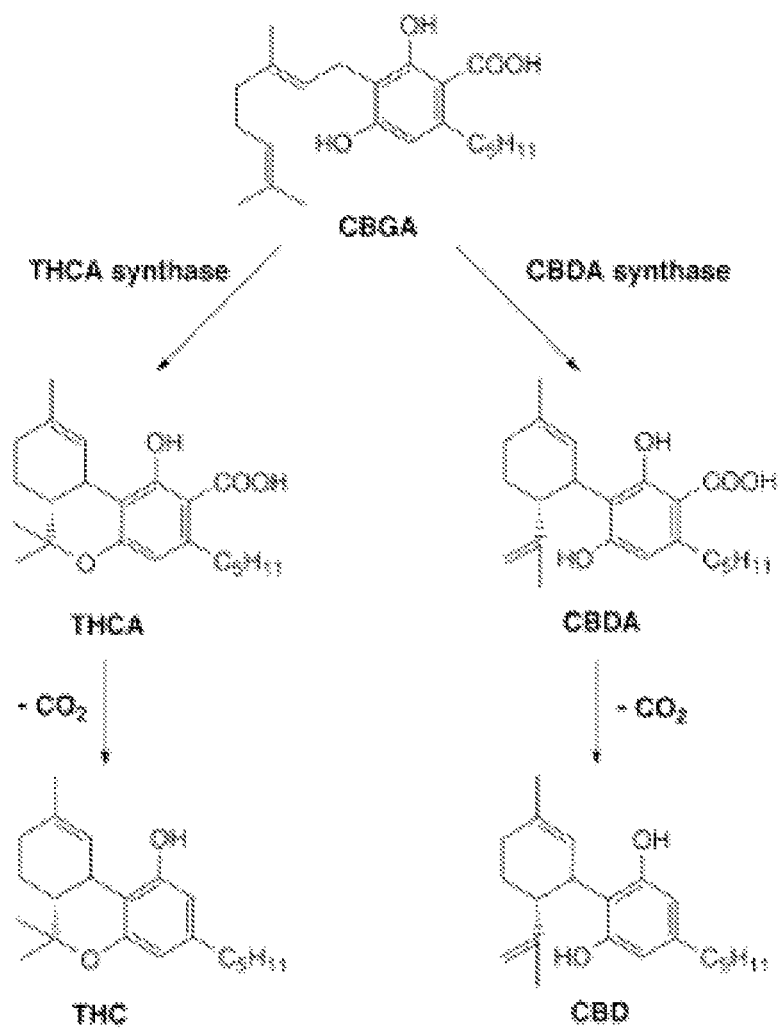
FIG. 1 describes a biosynthesis process for the production of THC and CBD
Figure 2:
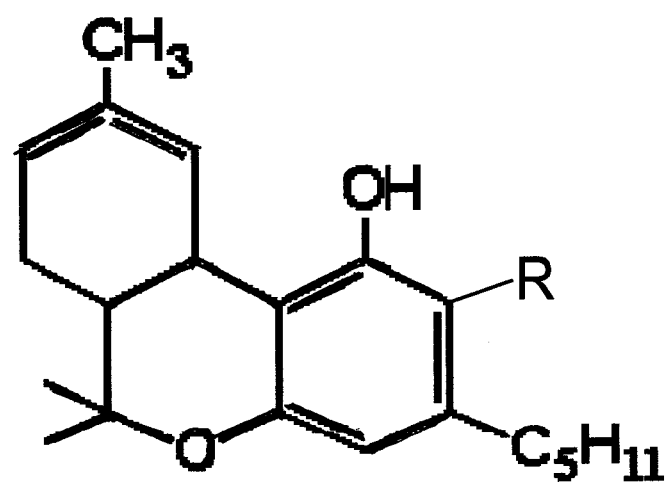
FIG. 2 describes a chemical structure of THC Acid A and THC.

The present invention provides a novel pharmaceutical composition of THC and CBD along with at least one small molecule, for effecting an increase in psychoactivity which is negated to provide enhanced therapeutic potency in regards to THC and/or CBD's ability of treating/preventing/ameliorating one or more disease(s) or condition(s) modulated by the activation of the Cannabinoid CB1 and/or CB2 receptors.

In an embodiment, the present invention provides a pharmaceutical composition comprising therapeutically effective amount of fully decarboxylated Δ9 Tetrahydrocannabinol (THC), Cannabidiol (CBD), and at least one small molecule, in selected ratios by weight.

In an embodiment, a ratio of THC:CBD (w/w) in the composition of the present invention ranges from 1:1 to 1:10. More preferably, the ratio of THC:CBD (w/w) ranges from 1:3 to 1:7.

In an embodiment, a ratio of THC:small molecule (w/w) in the composition of the present invention ranges from 1:0.1 to 1:10. More preferably, the ratio of THC:small molecule (w/w) ranges from 1:0.5 to 1:2.

In an embodiment, the composition further comprises of one or more of Cayenne Pepper, Papaya Powder, vanilla, *Cordyceps sinensis, Ganoderma lucidum, Pleurotis ostreatus, Hericeum Erinaceus*, or combinations thereof.

As used herein, "therapeutically effective amount" refers to administration of an amount of a given compound, to a subject in need thereof that achieves the desired therapeutic effect.

The term "subject" as used herein refers to a mammal, preferably a human.

The Applicant of the present invention has surprisingly found a novel relationship regarding psychoactivity in fully-decarboxylated THC, and discloses formation of the THC-based formulations/compositions which have greatly enhanced pharmacological action and exhibit a profound increase in psychoactivity. This increase in psychoactivity is negated by association of CBD one or more other small molecules.

In an embodiment, the present invention provides methods of treating one or more disease(s) or disorder(s) modulated by the activation of the Cannabinoid CB1 and/or CB2 receptors, by administering a therapeutically effective amount of the composition of the present invention to a subject in need thereof.

In one embodiment of the invention, the novel findings as described herein can be used to manipulate the endocannabinoid system into effecting an enhanced decrease in pain, as well as an enhanced sense of health, including an ability to more successfully overcome cancer.

In another embodiment of the present invention, Ascorbic acid, necessary for the hydroxylation of proline to hydroxyproline in the production of collagen in all tissues including the vessel walls, complements as one of the requisite small molecules in the compositions of the present composition.

In another embodiment, the composition as described herein has the capacity to reduce memory impairment as enhanced by inclusion of Lecithin as one of the small molecules, in addition to promoting enhanced cellular respiration, decreasing overall blood sugar to slow down the aging process, while decreasing pain. Since an organism's metabolism is based in large part upon its intake of Carbohydrate (C), Protein (P), Lipid (L), or combinations of CPL (or the lack thereof), diet can also influence the cell's overall response to inflammation by modulating respiration, in part through the Citric Acid Cycle which is located in mitochondria.

In an embodiment of the present invention, the THC-CBD composition along with glucose, Citric Acid, Ascorbic Acid or other small molecules as described herein, enter cells much faster by active and passive transport than THC-CBD formulations alone.

In one embodiment, the THC-based composition with CBD in association with one or more small molecules as described herein, exploits the connection between vaniloid receptors and the cellular uptake and enzymatic hydrolysis of anandamide (AEA) by enhancing already increased levels of endogenous AEA to positively mediate some pharmacological effects of THC and its analogues. In a further embodiment of the present invention, the THC-CBD composition along with citrus essential oils have much stronger, longer-lasting in-vivo effects, because formulations thusly derived effect potency by altering or delaying cyctochrome p450 enzme metabolism of THC and CBD.

In another embodiment, the composition of THC, CBD, and one or more small molecules, as described herein, promotes and maintains a more balanced metabolism at the intracellular-level by positively modulating the Citric Acid Cycle. In the cell, glucose is split into 2 equal parts and each is eventually converted to a molecule called pyruvate. This process is called glycolysis and the cell nets 2 ATP molecules (and 1 NAPH+H+). This occurs in the cytoplasm and does not require oxygen (anaerobic). The pyruvate molecules are transported into the mitochondria. Once in the matrix, these 3-carbon molecules (pyruvates) are prepared for the next step in which one of the three carbons is removed (decarboxylation) to become CO2. The remaining 2-carbon molecules (acetyl group) are primed with Coenzyme A. This acetyl-CoA molecule is bonded to the resident 4-carbon molecule (oxaloacetic acid) to form citric acid. The Citric Acid Cycle generates the following products through a series of steps including decarboxylation, phosphorylation etc. The main products for two turns of the cycle (one glucose molecule) are: 2ATP; 6 NADH+H+; 2 FADH2; and 4 CO2. The third and final phase of aerobic respiration is also located in the mitochondria—this time within the inner membranes, locked in place in a group of molecules collectively called the electron transport chain with associated proton pumps. The NADH2+ and FADH2 molecules give up their electrons to the electron transport chain molecules which in turn use this energy to move protons into the outer compartment. This sets up a free energy potential that is tapped by the F0F1 complexes in the same mitochondrial membrane to make ATP from ADP and Phosphate. The final electron acceptor in the electron transport chain is oxygen, thus creating a need to ingest water. Because the last step in aerobic respiration is the reaction of oxygen gas and hydrogen to form water as carried out by cytochrome oxidase, by increasing the need for intake of water into diet, efficiency of the Citric Acid Cycle is enhanced by heretoforth described utilization of fully-decarboxylated THC, CBD and one or more small molecules as described herein, at a selected defined ratios.

Because fully-decarboxylated THC is much more psychoactive when consumed in its fully-decarboxylated form as opposed to when it is consumed in its non-decarboxylated form, the compositions of the present invention provide increased therapeutic alternatives for systematic relief of a vast range of symptoms from organic issues including cancer, pain, glaucoma, neurodegeneration, Alzheimer's disease, Parkinson's disease, multiple sclerosis, and psychosis.

The pharmacological effects of the composition of the invention may be assigned to further areas of use as follows:

Appetite-stimulating effect: the appetite-stimulating effect of the composition of the invention can also be utilized therapeutically for anorexia/cachexia of HIV-positive patients (AIDS wasting) and for the postoperative changing of patients (especially those ventilated for a prolonged period) to oral nutrition.

Antiemetic (nausea-inhibiting) effect: the antiemetic effect of the composition of the invention can also be utilized to prevent nausea/vomiting resulting from chemotherapy (with a curative intent) in cancer patients (especially as adjuvant antiemesis during treatment with 5HT3 antagonists) and in antiemetic support therapy of HIV infection/AIDS and hepatitis B.

Antidepressant (mood-lightening) and anxiolytic (anxiety-reducing) effect: the antidepressant and anxiolytic effect of the composition of the invention can also be utilized for a supportive treatment of other chronic or (now) incurable disorders such as AIDS, paraplegia or chronic rheumatoid arthritis.

Other pharmacological effects of the composition of the invention are a sedative/sleep-promoting effect (sleeplessness), an antiepileptic effect (epilepsies), a bronchiodilating effect (bronchial asthma), a modulation of motor processes (neurological movement disorders such as, for example, dystonias, Tourette syndrome) and an anti-inflammatory (Inflammation-inhibiting) effect (Crohn's diseases, ulcerative colitis, arthritis, neurodermatitis).

As used herein, "pain" refers to nociceptive pain, Psychogenic pain or Neuropathic pain. In nociceptive pain, the stimulation of the sensory nerve endings, called nociceptors, causes the sensation of pain. Such pain often occurs after injury or surgery. The pain signals are transmitted by the nociceptors to the brain. Often the pain is localised, constant, and has an aching or throbbing quality. Once the damage to the tissue heals, the pain usually resolves. Psychogenic pain is a pain disorder that is associated with psychological factors. Headaches, muscle pains, back pain, and stomach pains are some of the most common types of psychogenic pain. Neuropathic pain is the result of an injury or malfunction of the peripheral or the central nervous system. The pain may be triggered by an injury but not necessarily by an injury of the nervous system itself. Neuropathic pain is frequently chronic. The pain relieving effect of the composition of the present invention on neuropathic pain should be particularly emphasized, for example, pain caused by migraine, disorders of the locomotor system, and of connective and muscle tissues (arthrosis, arthritis, myopathies), for painful menstruation, for gastrointestinal disorders (e.g. Crohn's disease) and for phantom pain.

Thus, in an embodiment, the present invention provides a method of treating/preventing/ameliorating a disease, disorder or condition selected from a group comprising of pain, cancer, pain, cancer, glaucoma, HIV, neurodegeneration, Alzheimer's disease, Parkinson's disease, multiple sclerosis, psychosis, anorexia/cachexia, nausea, hepatitis B, depression, anxiety, paraplegia, rheumatoid arthritis, sleeplessness, epilepsies, neurological movement disorders, Inflammation, Crohn's diseases, ulcerative colitis, arthritis, neurodermatitis cognitive impairment, dementia, diabetes mellitus and hypertension by administering a therapeutically effective amount of the composition to a subject in need thereof.

In one embodiment of the invention, the different therapeutic classes of medications that are useful to be used in addition to the composition of the present invention include but are not limited to, for example, natural opium alkaloids, anti-epileptics, non-selective monoamine reuptake inhibitors, opioids, anilides, diphenylpropylamine derivatives, acetic acid derivatives and related substances, platelet aggregation inhibitors excluding heparin, carboxamide derivatives, propionic acid derivatives, salicylic acid derivatives, local anaesthetics, non-steroidal anti-inflammatory or anti-rheumatic compounds, coxibs, topical non-steroidal anti-inflammatory compounds, opium alkaloids and derivatives, anaesthetics for topical use, drugs used in opioid dependence, hydantoin derivatives, oripavine derivatives, phenylpiperidine derivatives.

References to "THC or Δ9-tetrahydrocannabinol" and "Cannabidiol or CBD" or "cannabinoid(s)" as used herein, will be understood to also encompass pharmaceutically acceptable salts of such compounds. The term "pharmaceutically acceptable salts" refers to salts or esters prepared from pharmaceutically acceptable non-toxic bases or acids, including inorganic bases or acids and organic bases or acids, as would be well known to persons skilled in the art. Many suitable inorganic and organic bases are known in the art.

In an embodiment of the invention, THC and CBD may be present as plant extracts, as pure compounds, or a combination of the two. In a preferred embodiment, the cannabinoid extract of fully-decarboxylated THC and CBD is produced from at least one *Cannabis* plant, preferably organically-grown *Cannabis sativa*. Preferably the plant extract is in the form of a botanical drug substance.

In another preferred embodiment, the fully-decarboxylated THC as described herein comes from *Cannabis sativa* plants genetically-predisposed to be consistently high producers of relatively pure THC and CBD at a 1:1 ratio as source of the botanical drug substance THC.

In an embodiment, THC and CBD as used in the composition of the invention, can also be produced by a biosynthetic process, as reported in the literature and described herein FIG. 1, starting from Cannabigerolic Acid (CBGA) wherein CBGA is firstly converted to Cannabidiolic acid (CBDA) and Δ9-Tetrahydro-cannabinolic acid A (THCA) in the presence of enzymes CBDA synthase and THCA synthase, respectively, followed by decarboxylation by a non-enzymatic reaction to CBD and THC respectively.

The extracts as described herein can be prepared by processes well-known to a person skilled in the art, for example, maceration, percolation, extraction with subcritical or supercritical carbon dioxide, extraction with heated gases or solvents such as C1 to C5 alcohols (e.g. ethanol), Norflurane (HFA134a), HFA227. The extract may be further purified by subcritical or supercritical extraction, vaporisation and chromatography. When solvents such as those listed above are used the resultant extract may contain non-specific lipid-soluble material. This can be removed by a variety of processes including winterisation, which involves chilling to $-20°$ C. followed by filtration to remove waxy ballast, extraction with liquid carbon dioxide and by distillation.

The scope of the invention also extends to chemically-modified derivatives of fully-decarboxylated THC and CBD which retain desired activity, or more preferably natural derivates exhibiting improved activity which are produced according to standard principles of medicinal chemistry. By extension, fully-decarboxylated THC and CBD derivatives acceptable to this art may exhibit a lesser degree of activity than the starting material so long as they retain sufficient activity to be therapeutically effective or exhibit improvements in properties desirable in pharmaceutically active agents such as improved solubility, enhanced uptake or reduced toxicity. As such, fully-decarboxylated THC-CBD-based compositions of the present invention display profound solubility in aqueous buffers, enhanced in vivo uptake, and no toxicity.

In one embodiment, the composition of the present invention is prepared by following a general process comprising steps of:
(a) extracting fully decarboxylated THC and CBD from *Cannabis* Species or producing decarboxylated THC and CBD through biosynthesis process as reported in the literature;
(b) mixing THC and CBD as obtained from step (a) in a ratio of THC:CBD ranging from 1:1 to 1:10 by weight;
(c) adding one or more of the small molecule(s) to the mixture obtained from step (b); and
(d) mixing, pasteurizing and cooling the mixture obtained from step (c) to room temperature to obtain the composition.

In some embodiments, the pharmaceutical composition of the present invention is combined with other compounds or compositions known in the art such that the pharmaceutical composition is in the form of, for example, a pill, tablet, capsule or liquid form. The pharmaceutical composition may also be arranged to be injected, taken orally as a liquid or be in an aerosol form.

In some embodiments, the pharmaceutical composition as described herein is prepared to be administered in a variety of ways, for example orally or intravenously, using means known in the art. In other embodiments, the pharmaceutical composition may be administered as a patch.

In some embodiments of the present invention, the pharmaceutical composition as described herein may be combined with a pharmaceutically or pharmacologically acceptable carrier, binder, excipient or diluent, either biodegradable or non-biodegradable. See, for example, Remington: The Science and Practice of Pharmacy, 1995, Gennaro ed.

While the preferred embodiments of the invention have been described above, it will be recognized and understood that various modifications may be made therein, and the appended claims are intended to cover all such modifications which may fall within the spirit and scope of the invention.

In the following, the present invention is described in more detail by way of examples. However, these examples are not intended to limit the scope of protection of the present invention in any way.

EXAMPLES

Example 1

Preparation of the Pharmaceutical Composition

THC is extracted from *Cannabis sativa*, by subcritical $CO_2$, fully-decarboxylated, then heated to 44° C., mixed with CBD at a 1:1 ratio. The mixture so obtained is then mixed briefly with 1/10 to 1 volume (wt/wt) of a 50:50 mixture of Citric Acid:Ascorbic Acid. To this mixture is added 1/10 to 1/5 volume of vanilla, followed by addition of 1/10 to 1 volume of a mixture of Citrus Essential Oils composed of Orange Essential Oil, Tangerine Essential Oil, Grapefruit Essential Oil, Lime Essential Oil, or Lemon Essential Oil. To this is added, 1/20 to 1/10 volume of baking powder, 1/10 to 1/2 volume of Cayenne Pepper, 1/10 to 2 volumes of Papaya Powder, 1/10 to 1/5 volume of *Cordyceps sinensis* powder, 1/10 to 1/5 volume of *Ganoderma lucidum* powder, 1/10 to 1/5 volume of *Pleurotis ostreatus* powder, and 1/10 to 1/5 volume of *Hericeum Erinaceus*, followed by addition of 5 volumes of a combination of glucose-based sugar mix containing honey, powdered maple syrup, and other concentrated natural sugars. To this is added 1/4 to 1/2 volume Resvertrol, the preparation is mixed again, pasteurized (at 71° C. for 20 minutes), cooled to room temperature and packaged for distribution in the form of a capsule, pill, nasal spray container, or an eye dropper container.

What is claimed is:
1. A pharmaceutical composition comprising therapeutically effective amount of fully decarboxylated Δ9 Tetrahydrocannabinol (THC), Cannabidiol (CBD), and at least one small molecule, in selected ratios by weight, wherein the at least small molecule is selected from the group consisting of Citric Acid, Ascorbic Acid, Citrus Essential Oil(s), lecithin, one or more sugar(s), Resvertrol and combinations thereof; and
   one or more ingredients selected from the group consisting of: Cayenne Pepper, Papaya Powder, vanilla, *Cordyceps*

*sinensis, Ganoderma lucidum, Pleurotis ostreatus* or *Hericeum Erinaceus*, and combinations thereof.

2. The pharmaceutical composition of claim 1, wherein a THC:CBD ratio ranges from 1:1 to 1:10 by weight.

3. The pharmaceutical composition of claim 2, wherein the THC:CBD ratio ranges from 1:3 to 1:7 by weight.

4. The pharmaceutical composition of claim 1, wherein a THC:small molecule ratio ranges from 10:1 to 1:10 by weight.

5. The pharmaceutical composition of claim 4, wherein the THC:small molecule ratio ranges from 2:1 to 1:2 by weight.

\* \* \* \* \*